US007901628B2

(12) United States Patent
Yamamoto

(10) Patent No.: US 7,901,628 B2
(45) Date of Patent: Mar. 8, 2011

(54) METHOD FOR FRACTIONATING VARIOUS COMPONENTS CONTAINED IN A SAMPLE SOLUTION BY LIQUID CHROMATOGRAPH MASS SPECTROMETER

(75) Inventor: Yoshitake Yamamoto, Otakuni-gun (JP)

(73) Assignee: Shimadzu Corporation, Kyoto (JP)

( * ) Notice: Subject to any disclaimer, the term of this patent is extended or adjusted under 35 U.S.C. 154(b) by 579 days.

(21) Appl. No.: 12/078,220

(22) Filed: Mar. 28, 2008

(65) Prior Publication Data
US 2009/0001264 A1 Jan. 1, 2009

Related U.S. Application Data

(63) Continuation of application No. 10/606,230, filed on Jun. 26, 2003, now abandoned, which is a continuation-in-part of application No. 10/015,668, filed on Dec. 17, 2001, now abandoned.

(30) Foreign Application Priority Data

Sep. 30, 1999   (JP) .................................. H11-279167

(51) Int. Cl.
G01N 30/02 (2006.01)
H01J 49/00 (2006.01)
B01D 59/44 (2006.01)
G01N 15/06 (2006.01)

(52) U.S. Cl. ............ 422/70; 422/59; 422/68.1; 250/281; 250/282; 250/283; 250/285; 250/288

(58) Field of Classification Search .................. None
See application file for complete search history.

(56) References Cited

U.S. PATENT DOCUMENTS
6,469,297 B1 * 10/2002 Kato .............................. 250/288

* cited by examiner

Primary Examiner — Jill Warden
Assistant Examiner — Neil Turk
(74) Attorney, Agent, or Firm — Manabu Kanesaka

(57) ABSTRACT

A method for fractionating a sample solution includes the steps of setting a first mass spectrometry condition and mass range information; setting a second mass spectrometry condition and mass range information; executing a mass scan by the mass spectrum acquisition portion under the first mass spectrometry condition and obtaining first mass spectrum data; extracting first chromatogram data from the first mass spectrum data based on the first mass range information; executing a mass scan by the mass spectrum acquisition portion under the second mass spectrometry condition to obtain second mass spectrum data; extracting second chromatogram data from the second mass spectrum data based on the second mass range information; switching the first and second spectrometry conditions and repeating the mass scan cyclically; adding the first and second chromatograph data to obtain a chromatogram data; and operating the fraction collector based on the chromatogram data.

6 Claims, 9 Drawing Sheets

Fig. 4

| | Type | Start (min) | Stop (min) |
|---|---|---|---|
| 1 | | 0 | 10 |
| 2 | | 0 | 10 |
| 3 | | 0 | 0 |

Interface: Scan/SIM — MS

Analog Output
- Analysis Mode: Scan
- Sampling Rate: 1.5 sec.
- Detector Gain: 1.5 k.V
- Start m/z: 60
- Scan Width: [ ] amu
- Threshold: 0
- Stop m/z: 2000
- Scan Speed: 2000

MS Analysis Parameter

[OK] [Cancel] [Help]

METHOD FOR FRACTIONATING VARIOUS COMPONENTS CONTAINED IN A SAMPLE SOLUTION BY LIQUID CHROMATOGRAPH MASS SPECTROMETER

CROSS REFERENCE TO RELATED APPLICATION

This is a continuation application patent application Ser. No. 10/606,230 filed on Jun. 26, 2003, now abandoned, which is a continuation-in-part application of patent application Ser. No. 10/015,668 filed on Dec. 17, 2001, now abandoned.

BACKGROUND OF THE INVENTION AND RELATED ART STATEMENT

The invention relates to a method for fractionating various components contained in a sample solution by using a liquid chromatograph mass spectrometer.

Heretofore, there has been known a fraction chromatograph wherein a plurality of components contained in a sample is separated and collected by using a chromatograph device, such as high performance liquid chromatograph (hereinafter referred to as "HPLC").

FIG. 1 is a block diagram for showing an example of a structure of a fraction chromatograph using HPLC. An eluant, i.e. mobile phase, stored in an eluant tank 1 is sucked by a pump 2 and is transferred to flow into a column 4 through a sample introduction portion 3 at a predetermined flow rate. A sample solution injected into the mobile phase at the sample introduction portion 3 is introduced into the column 4 together with the mobile phase, and while passing through the column 4, components in the sample solution are separated and eluted.

A detector 5 detects the components eluted from the column 4 sequentially and sends detection signals to a signal process portion 6. All or a part of the eluate passing through the detector 5 is introduced into a fraction collector 8. The signal process portion 6 prepares a chromatogram based on the detection signals obtained from the detector 5, and a control portion 7 provides the fraction collector 8 with a control signal for fractionation based on a peak appearing on the chromatogram at real time. The fraction collector 8 controls an electromagnetic valve and the like based on the control signal, and distributes the eluate to vials corresponding to the respective components.

Recently, there has been widely used a liquid chromatograph mass spectrometer (hereinafter referred to as "LC/MS") using a mass spectrometer (hereinafter referred to as "MS") as a detector of HPLC. In the MS, various components contained in an introduced sample are separated and detected according to a mass number, i.e. mass/charge. Therefore, even if a plurality of components is overlapped at the same elution time, it is possible to separate these components for a qualitative analysis and a quantitative analysis.

FIG. 2 is a view showing an example of a configuration of the LC/MS apparatus. In the LC/MS, a mass scan is carried out within a certain mass range. Then, an intensity of an ion separated in every mass number is detected sequentially, and a relationship between the mass number and the intensity is created to obtain a mass spectrum. Also, a total ion chromatogram (hereinafter referred to simply as "chromatogram") can be obtained by repeatedly carrying out the mass scan, integrating the ion intensity in every scan regardless of the mass number and examining a change of the total ion intensity with time. Further, by focusing on a specific mass number, a mass chromatogram can be obtained by examining a change of the ion intensity having the mass number with time for every scan.

In general, in the LC/MS, a sample is ionized with a soft ionization method (an electro spray method, an atmospheric-pressure chemical ionization method and the like). Accordingly, different from an EI (electron impact) ionization method used in the GC/MS, it is possible to obtain a simple chromatogram in which only such ions as $[M+H]^+$ and $[M+Na]^+$, which are produced through an addition of a proton or a salt in the solvent to a material, are detected (hereinafter, called "molecular ion detection mode"). When it is necessary to obtain information regarding a molecular structure, a method called CID (collision induced dissociation) is used. In this method, a molecular ion is produced in a nebulizing chamber 11. Then, a voltage different from an ordinary voltage is applied to an electrode disposed in an immediate chamber 15 to induce the CID to create a fragment of the molecular ion, thereby detecting the fragment (hereinafter, called "fragment ion detection mode").

When the LC/MS is used for the fraction chromatograph, it is necessary to determine a timing of fraction based on chromatogram data for preparing a chromatogram or mass-chromatogram. Normally, the chromatogram data is calculated from a number of mass spectrum data obtained by a single mass scan according to a predetermined process condition set (for example, a sum of intensities of ions having a specific mass number, a sum of intensities of ions within a predetermined mass range and the like). Therefore, a single chromatogram data is obtained per a single mass scan.

When a mass scan is alternately switched between the molecular ion detection mode and the fragment ion detection mode within a wide mass range (for example, m/z: 20-2000) for the analysis, a chromatogram data obtained at a certain time point t is a value calculated based on the mass spectrum obtained in the molecular ion detection mode, and the subsequent chromatogram datum obtained at t+Δt is a value calculated based on the mass spectrum obtained in the fragment ion detection mode.

Generally, the background noises are at different levels in the molecular ion detection mode and the fragment ion detection mode. As a result, as shown in FIG. 7(a), a chromatogram based on a mass spectrum obtained in the molecular ion detection mode has a base line different from that of a chromatogram based on a mass spectrum obtained in the fragment ion detection mode. Therefore, as shown in FIG. 7(b), when the chromatogram data obtained whenever the mass scan is switched between the two measurement modes is continuously combined, a resultant chromatogram curve has a saw teeth shape.

Also, when a measurement is performed in a SIM mode in which only a predetermined mass number is continuously monitored to obtain a chromatogram, each chromatogram exhibits a chart like, for example, one shown in FIG. 8(a). As a result, as shown in FIG. 8(b), when the chromatogram data is continuously combined, a resultant chromatogram curve has a saw teeth shape.

In either case, it is difficult for the control portion 7 to accurately determine a starting point and a terminal point of a peak from such chromatogram data. Therefore, it is impossible to determine when each component should be fractionated, or an erroneous control signal is sent to the fraction collector 8. For this reason, when the conventional LC/MS is used for the fractionation operation, it is difficult to fractionate while alternately switching the measurement modes, and it is necessary to perform the fractionation operation in a single measurement mode, resulting in poor operational efficiency.

In view of the above problems, the present invention has been made, and an object of the present invention is to provide a liquid chromatograph mass spectrometer for obtaining a chromatogram to operate a fraction collector normally even when a mass spectrometry analysis is carried out while switching measurement conditions such as the molecular ion detection mode and the fragment ion detection mode. As a result, it is possible to complete a proper fractionation operation only through a single analysis.

Further objects and advantages of the invention will be apparent from the following description of the invention.

SUMMARY OF THE INVENTION

In order to solve the above-stated problems, according to the present invention, in a liquid chromatograph mass spectrometer, components in a sample are separated in a liquid chromatograph portion with time, i.e. along a passage of time. Then, the sample is introduced into a mass spectrum acquisition portion and a fraction collector, so that each component is fractionated and collected in the fraction collector based on information obtained in the mass spectrum acquisition portion.

The liquid chromatograph mass spectrometer includes: a setting device for setting a plurality of spectrometry conditions for mass spectrometry in advance; a spectrometry execution device for executing a cycle of the spectrometry while changing the spectrometry conditions set by the setting device whenever a single mass scan is carried out, and for repeating the spectrometry sequentially; an operation device for obtaining chromatogram data by adding a number of mass spectrum intensities obtained by the single mass scan whenever the cycle of the spectrometry is completed and further adding the sums of the respective mass scans, or for obtaining the chromatogram data by adding the mass spectrum data with respect to a specific mass number obtained by the respective mass scans; and a fraction control device for controlling an operation of the fraction collector based on the chromatogram data obtained by the operation device.

Here, the "spectrometry condition" is a condition that affects an ion generating condition or an ion detecting condition. The "spectrometry condition" includes, for example, a molecular ion detection mode and a fragment ion detection mode. When the setting device sets the molecular ion detection mode and the fragment ion detection mode, the spectrometry execution device alternately carries out a single mass scan in the molecular ion detection mode and a single mass scan in the fragment ion detection mode.

A large number of mass spectrum data with respect to the mass number is obtained per the single mass scan within a predetermined mass range. The operation device adds the mass spectrum intensities in the mass spectrum data per the single scan within a predetermined spectrum mass range. The spectrum mass range includes a range over the whole mass spectroscopy (TIC), a mass range arbitrary adjustable by an operator (MIC), and a range of a specific mass number (MI). The operation device further adds the sums of the mass spectrum intensities in the molecular ion detection mode and in the fragment ion detection mode to obtain a single chromatogram datum.

The single chromatogram datum contains mass spectrum data in a plurality of spectrometry conditions. Therefore, the single chromatogram datum is an averaged result even if the respective chromatograms have base lines at different levels depending on the spectrometry conditions, or a peak is present only in either of the spectrometry conditions. Incidentally, when the fractionation operation is carried out based on the mass chromatogram, the operation device adds the mass spectrum data with respect to a specific mass number obtained by each mass scan to obtain the chromatogram data.

According to the liquid chromatograph mass spectrometer of the present invention, even when the mass scan is carried out while switching the spectrometry conditions of the mass spectrometry, it is possible to obtain the chromatogram having a normal peak waveform. Therefore, it is possible to fractionate the respective components with the fraction collector.

BRIEF DESCRIPTION OF THE DRAWINGS

FIG. 4 is a view showing a screen for setting a spectrometry condition;

DETAILED DESCRIPTION OF PREFERRED EMBODIMENTS

Figure 1:
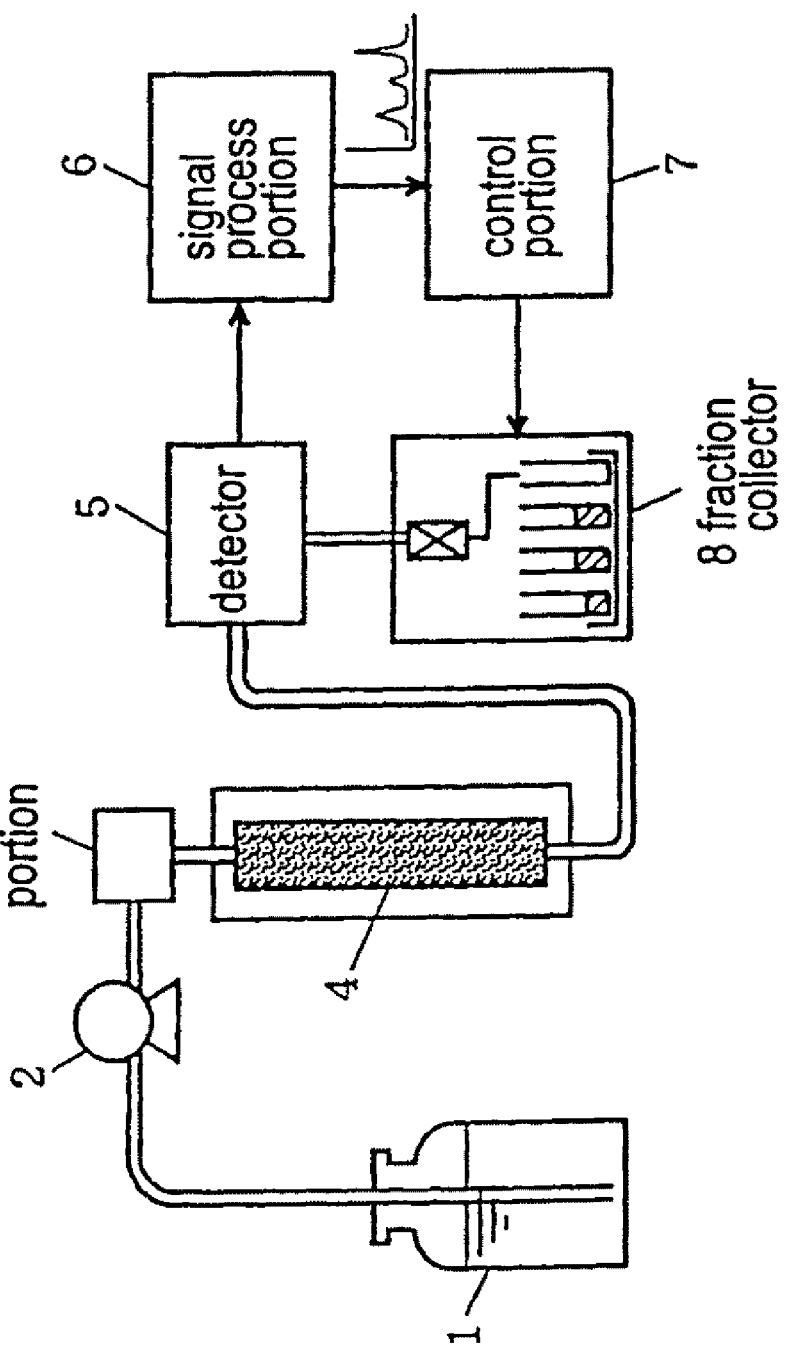
FIG. 1 is a block diagram showing a structure of a conventional fraction chromatograph using a general HPLC.
Figure 2:
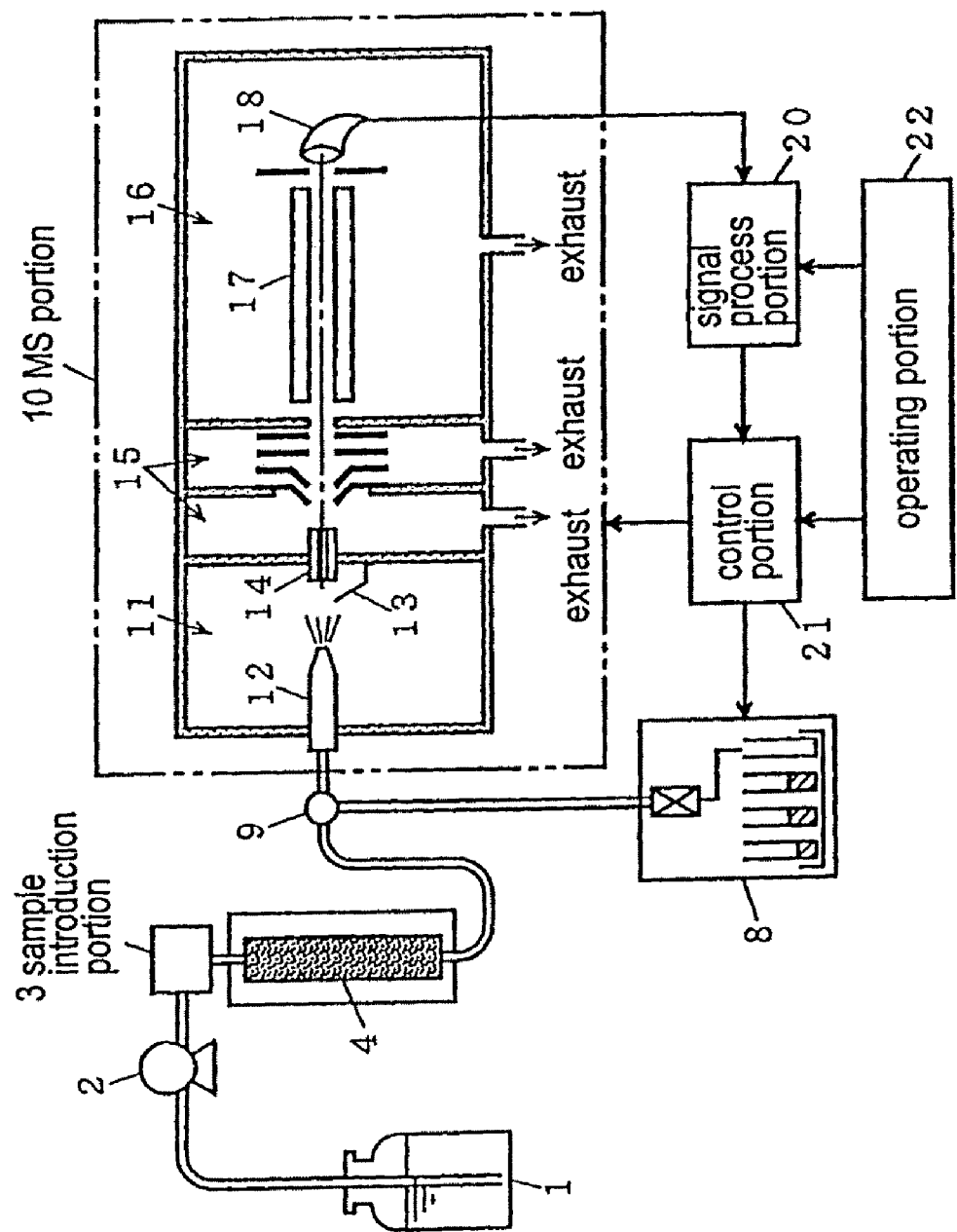
FIG. 2 is a block diagram showing an entire structure of LC/MS according to the present invention.

Hereunder, embodiments of the present invention will be explained with reference to the accompanying drawings. In the LC/MS of the invention, a sample is ionized with a soft ionization method (an electro spray method, an atmospheric-pressure chemical ionization method and the like). FIG. 2 is a block diagram of an entire LC/MS according to the present embodiment in a case that an atmospheric-pressure chemical ionization method (APCI) is used.

A sample solution is eluted from a column 4 of an LC, and then divided in two-flow paths at a predetermined ratio at a flow-path branch portion 9. One of the sample solutions is sent to an MS portion 10 and the other is sent to a fraction collector 8. The MS portion 10 includes a nebulizing or atomizing chamber 11 having a nozzle 12 and a discharge electrode 13, and a spectrometry chamber 16 having a quadrupole filter 17 and an ion detector 18. Two intermediate chambers 15 are provided between the nebulizing chamber 11 and the spectrometry chamber 16. The nebulizing chamber 11 is connected to the first intermediate chamber 15 through a de-solvent pipe 14.

The ion detector 18 in the MS portion 10 sends a detection signal to a signal process portion 20. After the signal is processed at the signal process portion 20 (described later), the chromatogram data is sent to a control portion 21. The control portion 21 controls operations of the respective portions in the MS portion 10, the fraction collector 8, and the respective portions of the LC (a control signal line is not shown).

An operation of the MS portion 10 will be explained as follows. When the sample solution supplied from the column 4 reaches the nozzle 12, the sample solution is sprayed in the nebulizing chamber 11 as high temperature drops. The sprayed drops collide with gas molecules under the atmospheric pressure to break down into further fine drops, and are quickly dried, i.e. removal of the solvent, to thereby vaporize the sample molecules. The fine gas particles contact buffer ions produced by the corona discharge from the discharge electrode 13 to cause a chemical reaction, and are ionized.

The fine drops containing the generated ions plunge into the de-solvent pipe 14, and the solvent is further removed while the fine drops pass through the de-solvent pipe 14. The ions are sent to the spectrometry chamber 16 through the two intermediate chambers 15, and only target ions having a specific mass number, i.e. mass/charge, pass through the quadrupole filter 17 disposed in the spectrometry chamber 16 to reach the ion detector 18. The ion detector 18 retrieves an electric current corresponding to the ion number of the ions arrived at the ion detector 18.

In the MS portion 10, a voltage applied to the respective portions such as the discharge electrode 13 is changed. Also, it is possible to switch between a molecular ion detection mode and a fragment ion detection mode, or between positive/negative ion detection modes, by switching the operation of the ion detector 18.

Hereunder, an operation of the LC/MS will be explained when the fractionation operation is performed under the spectrometry condition for switching between the molecular ion detection mode and the fragment ion detection mode.

Figure 3:
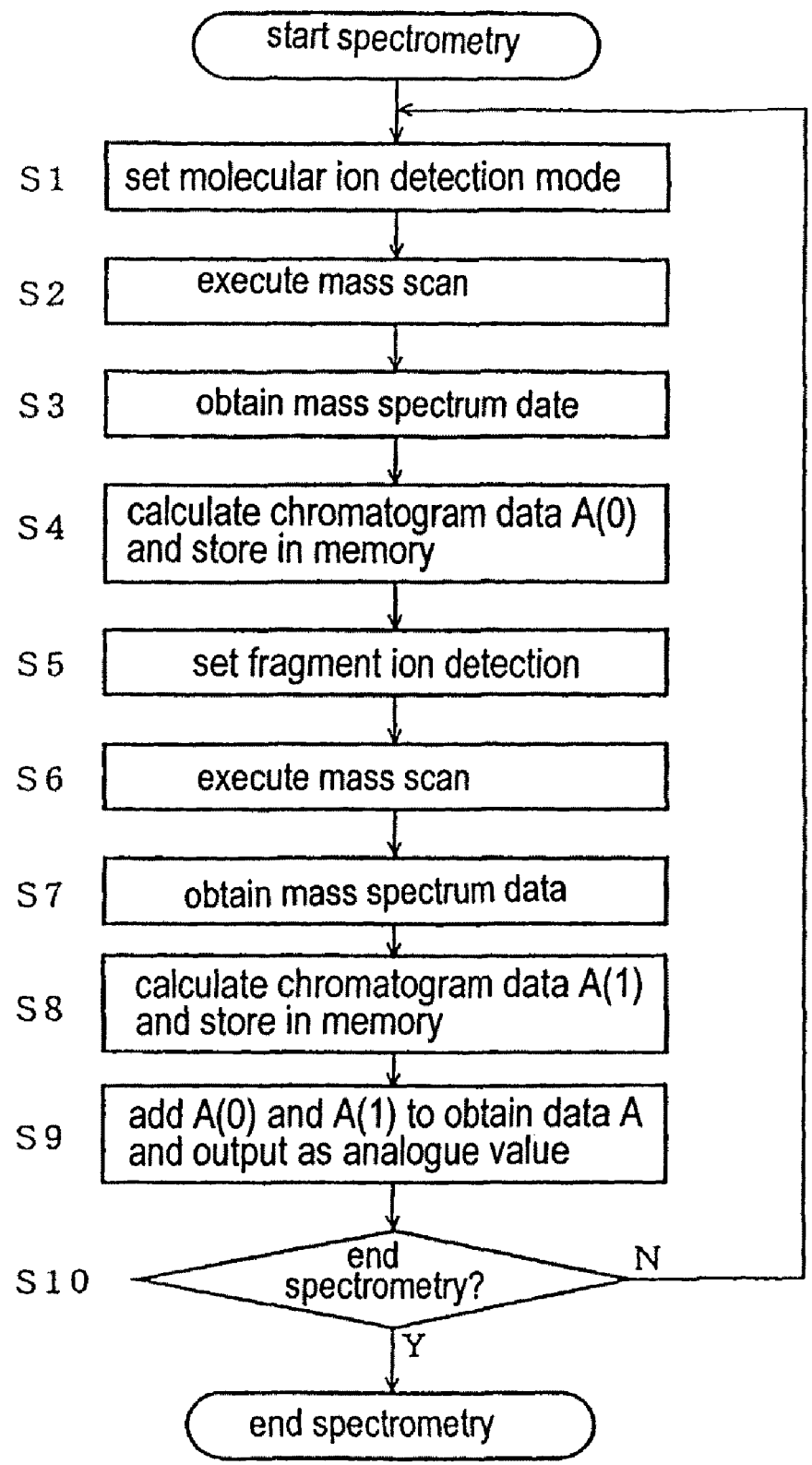
FIG. 3 is a flow chart showing a signal process operation.
Figure 6:
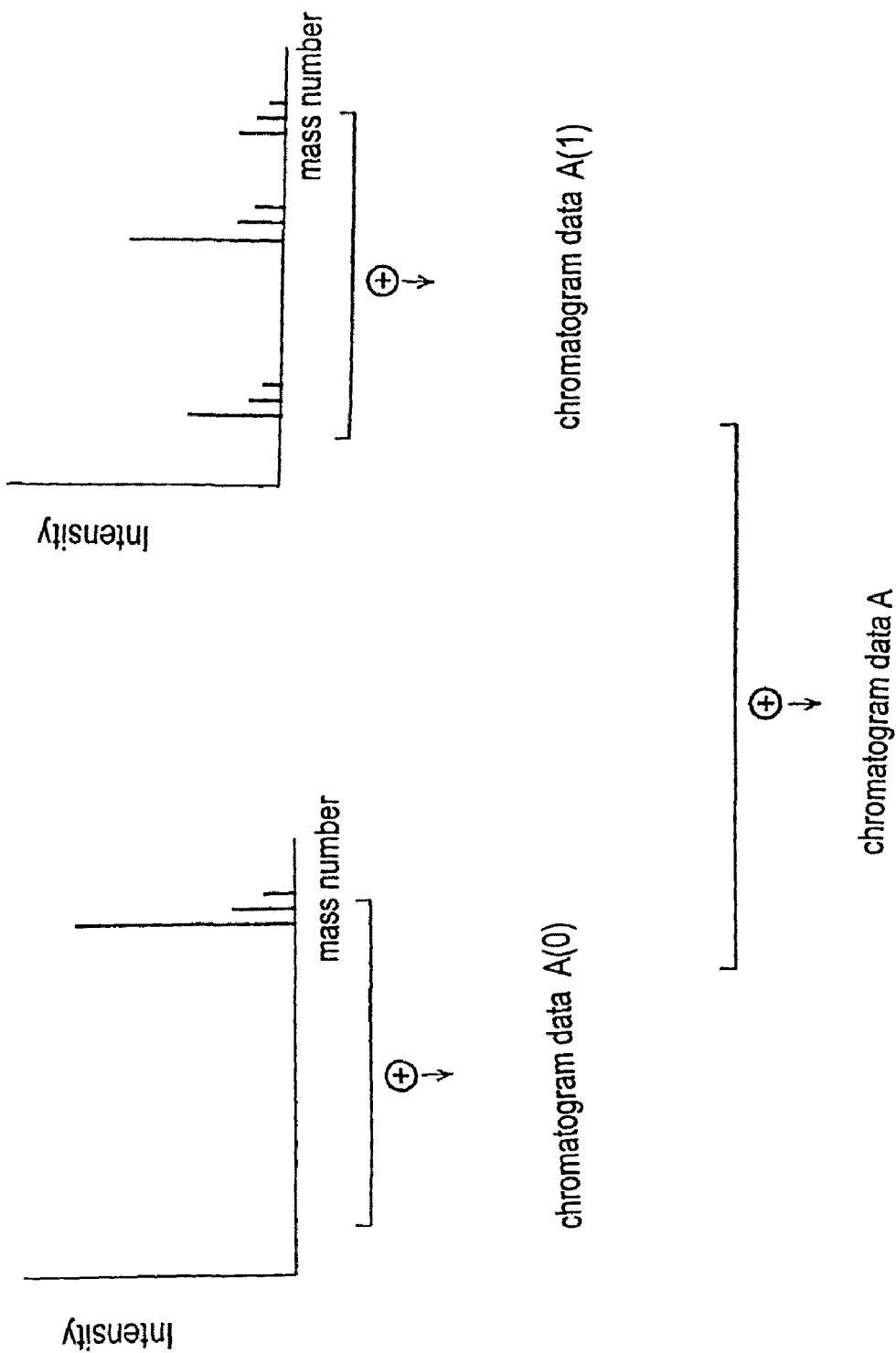
FIG. 6 is a graphic chart for explaining a signal process operation.

FIG. 3 is a flow chart showing operations at the time of the spectrometry in the signal process portion 20 and the control portion 21, FIG. 4 is a view showing a screen for setting the spectrometry condition, and FIG. 6 is a graphic chart for explaining the operation. An operator inputs various parameters through the operating portion 22 such as an operation condition of LC, an operation condition of the MS portion 10 and a process condition in the signal process portion 20.

Figure 5:
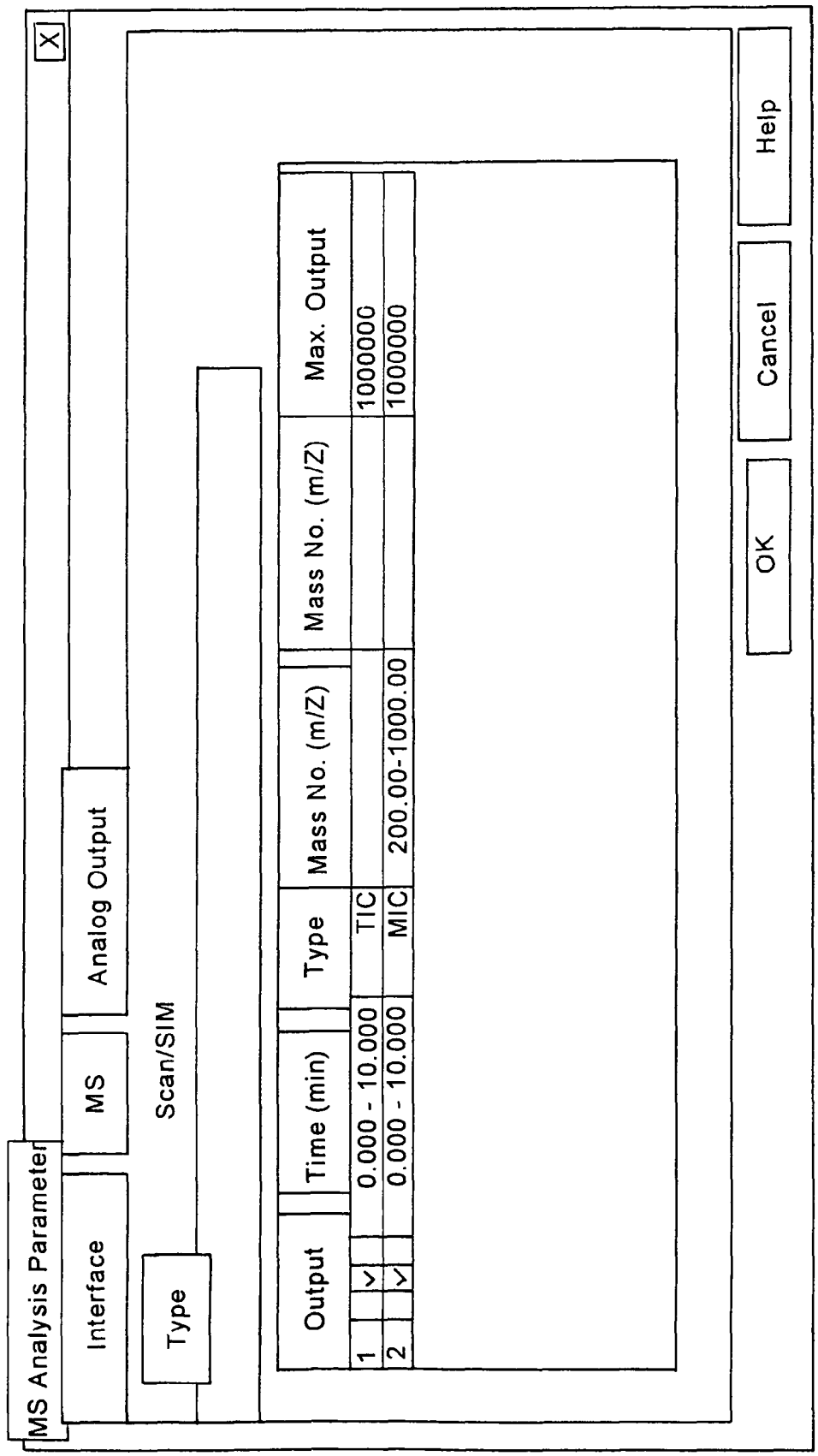
FIG. 5 is a view showing a screen for setting an analog output condition.

As shown in FIG. 4, a plurality of spectrometry conditions having the same start/stop time is created to repeat the spectrometry set in the operating portion 22. FIG. 5 is a view showing an example of a screen for inputting an analog output condition. According to the mass spectrometry conditions created in FIG. 4, the operator inputs mass range information and a coefficient of conversion to a voltage value for calculation to control the fraction collector. The mass range information includes a range over the whole mass spectroscopy (TIC), a mass range arbitrary adjustable by an operator (MIC), and a range of a specific mass number (MI). In this embodiment, it is arranged that two mass ranges can be added to obtain the chromatogram data from a single mass spectrum. When there are more than two ranges, it is still possible to add the specified ranges.

When the spectrometry starts, first, the control portion 21 sets parameters of the respective portions of the MS portion 10 for the molecular ion detection mode (Step S1), and carries out the mass scan in a predetermined mass range (Step S2). At the time of the mass scan, when the voltage applied to the quadrupole filter 17 is scanned, the mass number of the ions passing through the quadrupole filter 17 to reach the ion detector 18 is changed.

The signal process portion 20 processes the detection signals changing sequentially during the mass scan, and obtains the mass spectrum data representing a relationship between the mass number and the ion intensity (Step S3). Among a large number of mass spectrum data, the mass spectrum data is extracted according to the predetermined process conditions (mass range information). The mass spectrum is added together to obtain the chromatogram data A(0) of the molecular ion detection mode, and the chromatogram data is stored in a memory (Step S4).

Then, the control portion 21 sets parameters of the respective portions of the MS portion 10 for the fragment ion detection mode (Step S5), and carries out the mass scan in a predetermined mass range (Step S6). More specifically, the control portion 21 carries out the mass scan in the same manner as in the above-explained molecular ion detection mode. The signal process portion 20 processes the detection signals changing sequentially during the mass scan to obtain the mass spectrum data representing a relationship between the mass number and the ion intensity (Step S7). Among a large number of the mass spectrum data, the mass spectrum data is extracted according to the predetermined process conditions. The mass spectrum data is added together to obtain the chromatogram data A(1) of the fragment ion detection mode (Step S8).

After the chromatogram data A(0) and A(1) are obtained, both data are added together to obtain the chromatogram data A and outputted as an analogue value (Step S9). Thereafter, until the spectrometry for all components is completed, the above-described process returns to Step S1 from Step S10 to repeat.

Figure 7A:
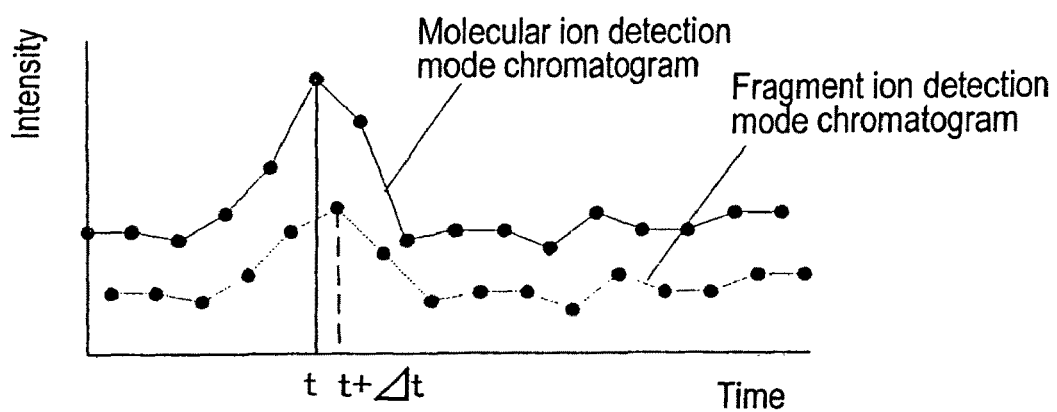
FIGS. 7(a) and 7(b) are chromatograms for explaining problems in a fraction device using a conventional LC/MS.
Figure 7B:
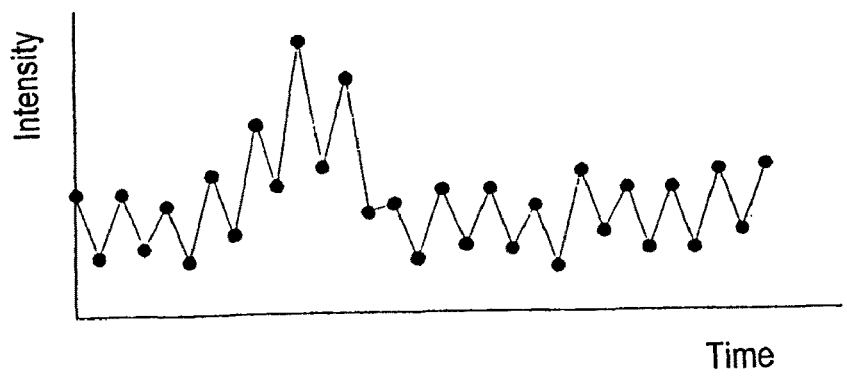
Figure 8A:
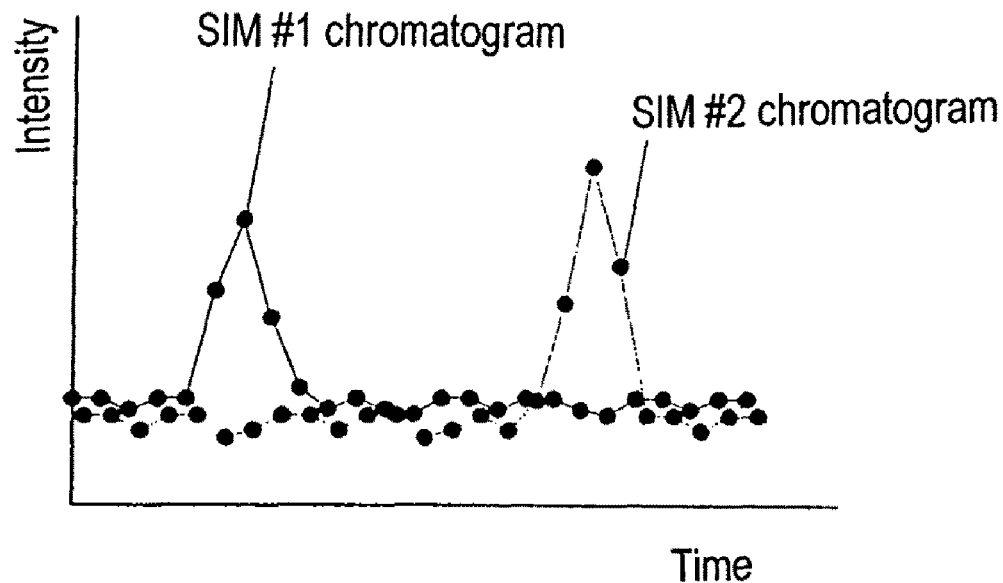
FIGS. 8(a) and 8(b) are other chromatograms for explaining problems in a fraction device using a conventional LC/MS.
Figure 8B:
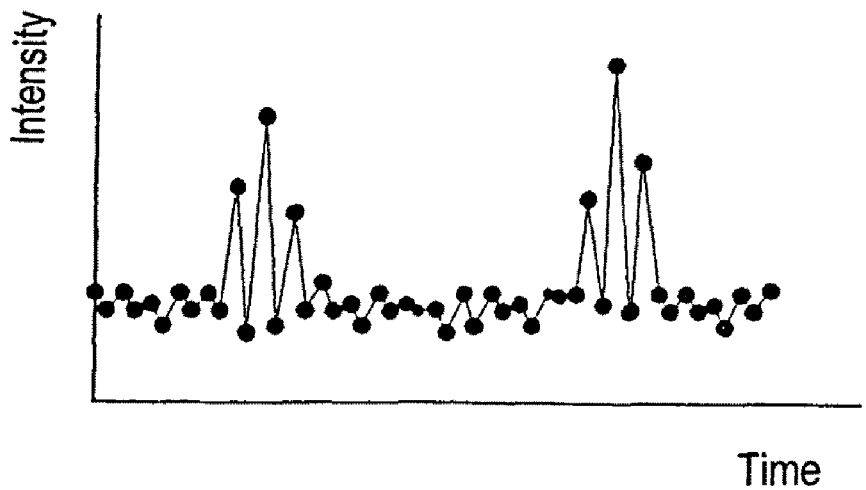
Figure 9A:
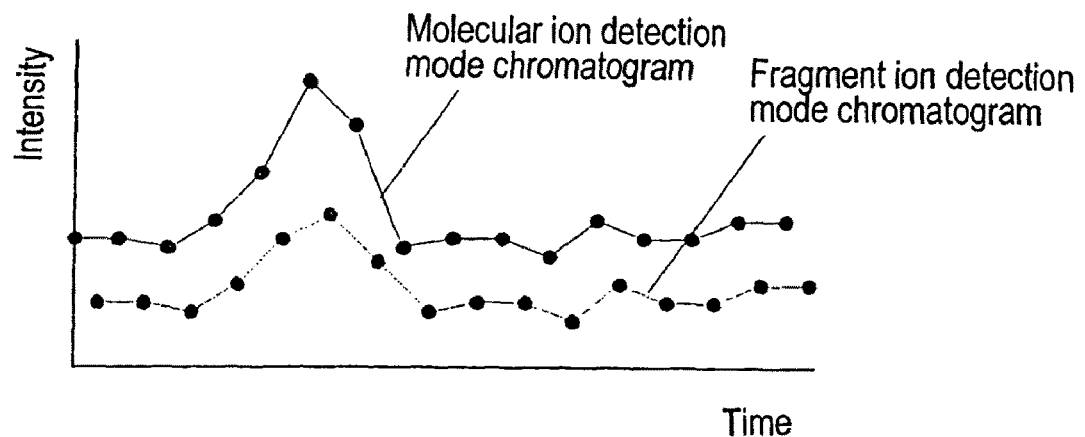
FIGS. 9(a) and 9(b) are examples of chromatograms obtained in an embodiment of the present invention.
Figure 9B:
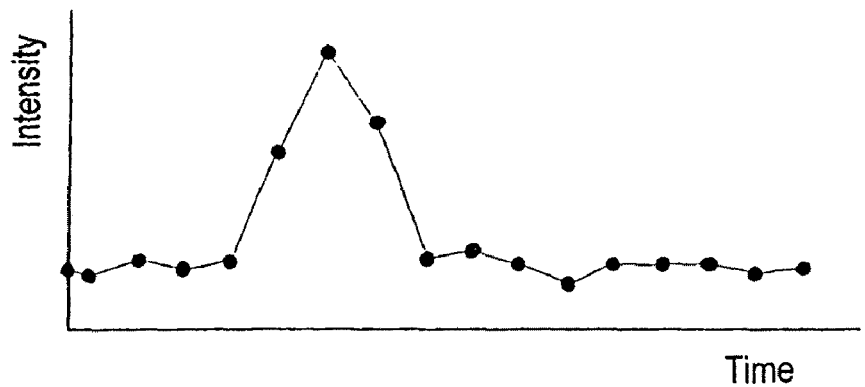

With the above-described process, as shown in FIG. 6, one chromatogram datum A is obtained per two mass scans. FIGS. 9(a) and 9(b) are the chromatograms based on the chromatogram data obtained from the signal process portion 20. As shown in FIG. 9(a), the two chromatograms in the molecular ion detection mode and the fragment ion detection mode are obtained separately, and the two chromatograms have different intensity levels. As shown in FIG. 9(b), in the LC/MS of the invention, a peak of the chromatogram appears in a normal form, not in the saw teeth shape shown in FIG. 7(b).

When the control portion 21 receives the chromatogram data from the signal process portion 20 at a real time, the control portion 21 detects a starting point of a peak of an objective component to be fractionated, and outputs a collection start signal to the fraction collector 8 with a predetermined time delay from the time when the starting point is detected. The time delay is determined according to a flow rate of a mobile phase and a pipe capacity from the flow path branch portion 9 to the nozzle 12 of the MS portion 10 and from the flow path branch portion 9 to an electromagnetic valve of the fraction collector 8.

In the fraction collector 8, when the objective component reaches the electromagnetic valve, the electromagnetic valve is opened according to the collecting start signal to start the fractionation. When a termination point of the peak of the objective component is detected, the control portion 21 sends a collection completion signal to the fraction collector 8 in the same manner. When the fractionation or separation of the objective component is completed, the electromagnetic valve is closed. In a case that a plurality of components is fractionated, during a period when the electromagnetic valve is closed, a vial bottle is moved by a biaxial arm or the like and an empty vial bottle is set at a fractioning position for the next component.

As described above, the spectrometry is carried out using a plurality of the spectrometry conditions. When the single chromatogram is used to process the fraction collector, a box of output control on the screen shown in FIG. 5 is unchecked. Accordingly, the spectrometry condition is created without using the data for the calculation, so that either of the chromatogram data A(0) and A(1) is treated as zero during the process shown in FIG. 3.

In the embodiment, the molecular ion detection mode and the fragment ion detection mode are processed alternately. Alternatively, the alternately switching method can be used for changing or switching other various operation conditions of the mass spectrometry. For example, it is possible to perform the analysis while changing polarity of the ion to be detected. When there are more than three operation conditions, a single chromatogram datum may be obtained in every more than three mass scans according to the operation conditions.

While the invention has been explained with reference to the specific embodiments of the invention, the explanation is illustrative and the invention is limited only by the appended claims.

What is claimed is:

1. A method for fractionating various components contained in a sample solution using a liquid chromatograph mass spectrometer after separating the sample into the components along a passage of time by a liquid chromatograph portion, and subsequently introducing the components to a mass spectrum aquisition portion and a fraction collector, comprising the steps of:

setting a first mass spectrometry condition and first mass range information for determining the components to be separated;

setting a second mass spectrometry condition and second mass range information for determining the components to be separated;

carrying out a first mass scan on the separated components by the mass spectrum acquisition portion under the first spectrometry condition and obtaining first mass spectrum data;

extracting first chromatogram data from the first mass spectrum data based on the first mass range information;

carrying out a second mass scan on the separated components by the mass spectrum acquisition portion under the second mass spectrometry condition to obtain second mass spectrum data;

extracting second chromatogram data from the second mass spectrum data based on the second mass range information;

switching the first and second spectrometry conditions and cyclically repeating the first and second mass scans;

adding the first and second chromatograph to obtain combined chromatogram data during a predetermined time period for analysis; and diverting the separated components in the fraction collector based on the combined chromatogram data to obtain fractionated components when said data indicates an objective component is present in the sample solution.

2. A method according to claim 1, wherein a control portion is connected to the mass spectrum acquisition portion for executing a cycle of the mass spectrum acquisition while changing the plurality of spectrometry conditions set by an operating portion, said control portion sequentially executing the mass scan repeatedly, and a signal process portion adds spectrum intensities obtained in the plurality of spectrometry conditions whenever one cycle of the mass spectrometry is completed to obtain chromatogram data, said fraction collector collecting the fractionated components based on the chromatogram data obtained by the signal process portion.

3. A method according to claim 1, wherein said chromatograph mass spectrometer is a liquid chromatograph mass spectrometer.

4. A method according to claim 2, wherein said control portion executes the mass spectrum in a molecular ion detection mode and a fragment ion detection mode alternately.

5. A method according to claim 2, wherein the plurality of spectrometry conditions are different ionization modes.

6. A method according to claim 2, wherein the control portion detects a starting point of a peak of an objective component.

* * * * *